United States Patent
Lu et al.

(10) Patent No.: US 11,981,638 B2
(45) Date of Patent: May 14, 2024

(54) PHENYL AMINO SODIUM PROPIONATE DERIVATIVE, PREPARATION METHOD THEREFOR AND APPLICATION THEREOF

(71) Applicant: SHENZHEN CHIPSCREEN BIOSCIENCES CO., LTD., Guangdong (CN)

(72) Inventors: Xianping Lu, Guangdong (CN); Zhibin Li, Guangdong (CN); Xianghui Wang, Guangdong (CN); Weijun Gao, Guangdong (CN); Xingyu Deng, Guangdong (CN)

(73) Assignee: SHENZHEN CHIPSCREEN BIOSCIENCES CO., LTD., Guangdong (CN)

( * ) Notice: Subject to any disclaimer, the term of this patent is extended or adjusted under 35 U.S.C. 154(b) by 825 days.

(21) Appl. No.: 17/053,364

(22) PCT Filed: Apr. 29, 2019

(86) PCT No.: PCT/CN2019/084921
§ 371 (c)(1),
(2) Date: Nov. 6, 2020

(87) PCT Pub. No.: WO2019/214482
PCT Pub. Date: Nov. 14, 2019

(65) Prior Publication Data
US 2021/0078948 A1    Mar. 18, 2021

(30) Foreign Application Priority Data
May 9, 2018  (CN) .......................... 201810437901.5

(51) Int. Cl.
C07D 209/86 (2006.01)
G01N 1/28 (2006.01)
G01N 30/02 (2006.01)
G01N 30/06 (2006.01)

(52) U.S. Cl.
CPC ............. *C07D 209/86* (2013.01); *G01N 1/28* (2013.01); *G01N 30/06* (2013.01); *G01N 2001/2893* (2013.01); *G01N 2030/027* (2013.01); *G01N 2030/062* (2013.01)

(58) Field of Classification Search
None
See application file for complete search history.

(56) References Cited

U.S. PATENT DOCUMENTS

| | | |
|---|---|---|
| 7,268,157 B2 | 9/2007 | Lu et al. |
| 2019/0225582 A1 | 7/2019 | Lu et al. |
| 2020/0031771 A1 | 1/2020 | Yu et al. |

FOREIGN PATENT DOCUMENTS

| | | |
|---|---|---|
| CA | 3038381 A1 | 4/2018 |
| CN | 1562970 A | 1/2005 |
| CN | 105801468 A | 7/2016 |
| CN | 107868033 A | 4/2018 |
| JP | 2006519171 A | 8/2006 |
| RU | 2157803 C2 | 10/2000 |
| TW | 201813955 A | 4/2018 |
| TW | 201813956 A | 4/2018 |
| WO | 2004048333 A1 | 6/2004 |
| WO | 2016107222 A1 | 7/2016 |
| WO | 2018059427 A1 | 4/2018 |

OTHER PUBLICATIONS

Erturk et al, Journal of Pharmaceutical and Biomedical Analysis, vol. 33, pp. 1017-1023 (Year: 2003).*
First Office Action dated Mar. 3, 2022 for Chinese patent application No. 201810437901.5, English translation provided by Global Dossier.
Second Examiner's Report dated Jan. 13, 2023 for Canadian patent application No. 3,099,503.
Taijun Hang et al., "Medicine Analysis", Beijing: People's Health Publishing House, 7th Edition, Aug. 2011, p. 97-99, p. 135-142, Aug. 31, 2011.

(Continued)

*Primary Examiner* — Zinna Northington Davis
(74) *Attorney, Agent, or Firm* — Yue (Robert) Xu; Apex Attorneys at Law, LLP

(57) ABSTRACT

Disclosed are a phenyl amino sodium propionate derivative, a preparation method therefor and an application thereof. Specifically, disclosed are sodium 3-(4-(2-(9H-carbazole-9-yl)ethoxy)phenyl)-2-((2-(4-(4-(2-sodium forrnate-2-((2-(4-fluorobenzoyl)phenyl)amino)ethyl)phenoxy)benzoyl)phenyl)amino)propionate, a preparation method therefor and the use thereof for quality control of a bulk drug or formulation of Chiglitazar or a derivative thereof. Particularly, the compound can be used as a control substance or standard substance for the detection of impurities/related substances in Chiglitazar or a sodium salt drug thereof.

9 Claims, No Drawings

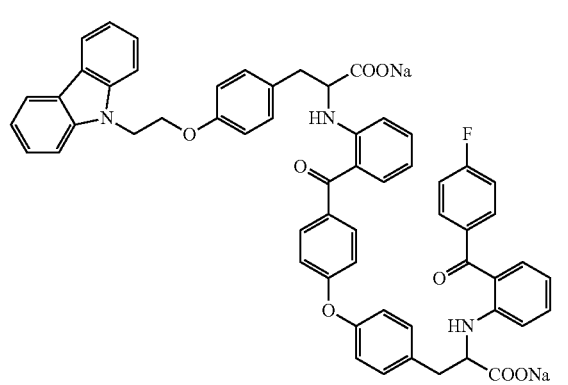

(I)

(56) References Cited

OTHER PUBLICATIONS

Liu et al., "Quantification of Chiglitazar and its Related Substances by HPLC", Chinese Journal of New Drugs, 15, pp. 458-461, 2006.
First Office Action dated Apr. 22, 2021 for Russian patent application No. 2020139828, English translation provided by Unitalen.
First Office Action dated Jan. 20, 2022 for Canadian patent application No. 3,099,503.
First Office Action dated Nov. 24, 2021 for Japanese patent application No. 2020-562699, English translation provided by Global Dossier.
International Search Report for PCT/CN2019/084921 mailed Jul. 1, 2019, ISA/CN.

* cited by examiner

PHENYL AMINO SODIUM PROPIONATE DERIVATIVE, PREPARATION METHOD THEREFOR AND APPLICATION THEREOF

CROSS REFERENCE TO RELATED APPLICATIONS

The present application is a US National Phase application based upon PCT Application No. PCT/CN2019/084921, filed Apr. 29, 2019, which claims the priority of Chinese Patent Application No. 201810437901.5, filed to the China National Intellectual Property Administration on May 9, 2018, and titled "PHENYL AMINO SODIUM PROPIONATE DERIVATIVE, PREPARATION METHOD THEREFOR AND APPLICATION THEREOF", the content of which is incorporated herein by reference in its entirety.

FIELD

The present disclosure belongs to the field of chemical pharmacy, in particular to a phenyl amino sodium propionate derivative, a preparation method therefor and a use thereof for quality control of an active pharmaceutical ingredient/bulk drug or formulation of Chiglitazar or a derivative thereof. In particular, the phenyl amino sodium propionate derivative can be used as a control or standard substance for the detection of impurities or related substances in a bulk drug or formulation of Chiglitazar or a salt thereof (for example, a sodium salt).

BACKGROUND 2-(2-(4-fluorobenzoyl)phenylamino)-3-(4-(2-(9H-carbazole-9-yl)ethoxy)phenyl)propionic acid, commonly known as Chiglitazar, is a phenylalanine compound which has a therapeutic and prophylactic activity against metabolic diseases, the chemical structural formula thereof is as follow:

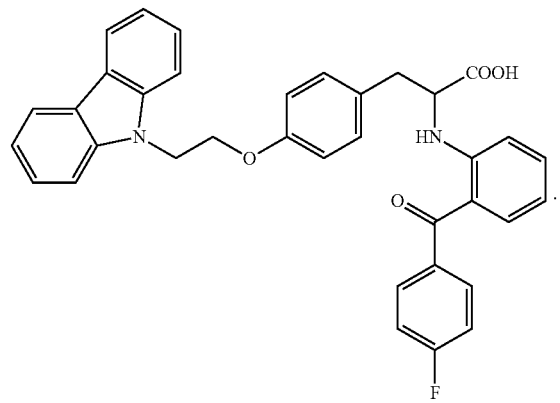

The pharmacological activity of this compound is described in both Chinese Patent Application CN03126974.5 and U.S. Pat. No. 7,268,157. Chiglitazar has the ability to activate PPAR-α, PPAR-γ and PPAR-δ selectively, and can be used to treat diseases associated with metabolic syndrome such as diabetes, hypertension, obesity, insulin resistant syndrome, hypertriglyceridemia, hyperglycemia, high cholesterol, atherosclerosis, and coronary artery heart disease.

In the prior art, the synthesis of Chiglitazar and a sodium salt thereof is disclosed in Chinese Patent Application No. 201610855107.3 and Chinese Patent Application No. 201410856282.5.

An industrial method for producing Chiglitazar is disclosed in Chinese Patent Application No. 201610855107.3, and the synthetic route is as follows:

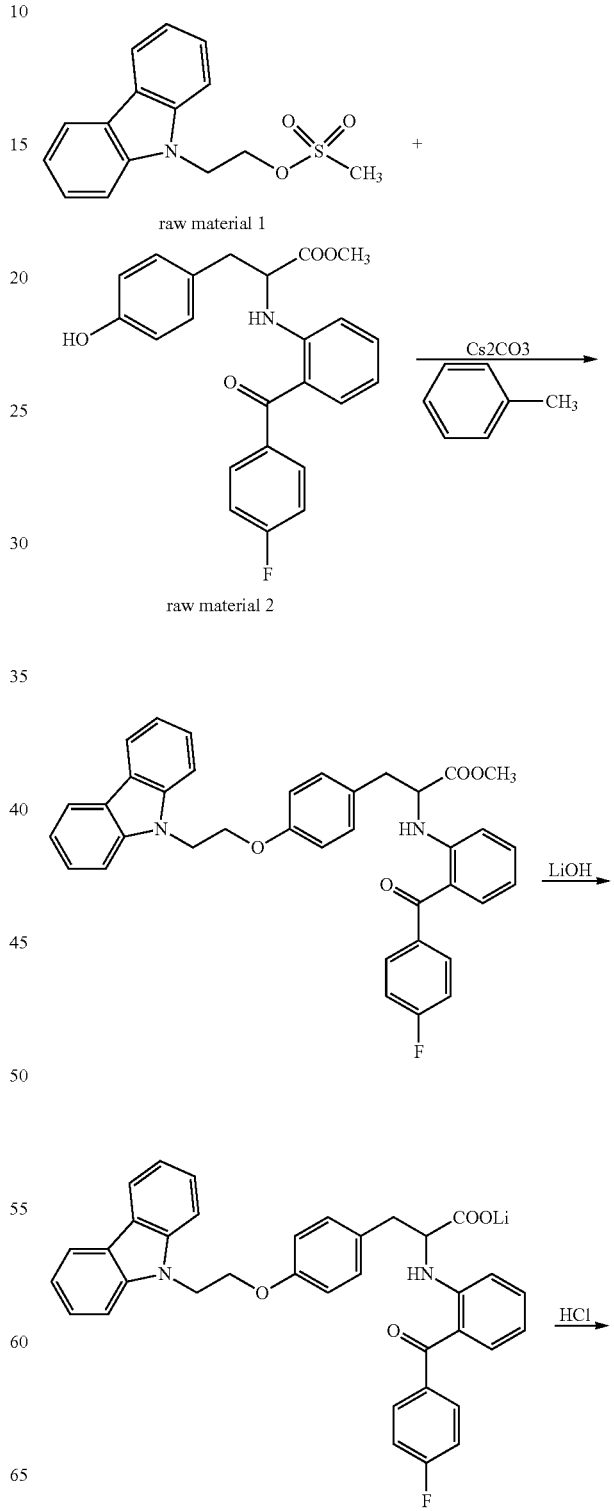

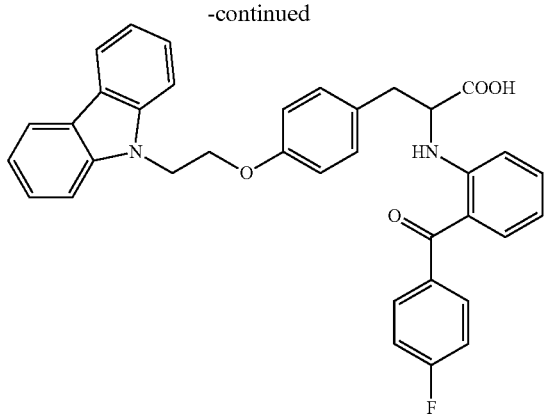

This method is suitable for industrial production, and the target compound obtained has high purity. However, since Chiglitazar has poor stability and is easy to decompose during manufacture, storage and transportation which seriously affects safety and effectiveness of the drug. It is necessary to prepare Chiglitazar in a form of sodium salt which has better stability, i.e., Chiglitazar sodium. A method for producing Chiglitazar sodium is disclosed in Chinese Patent Application No. 201410856282.5 as follows:

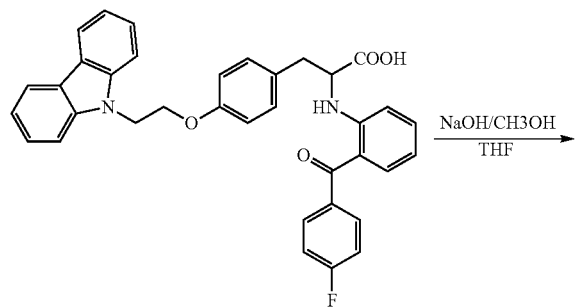

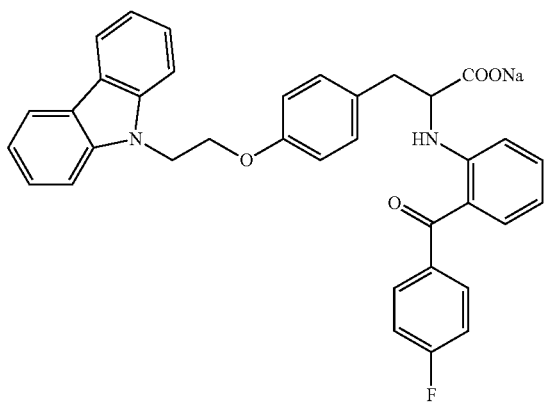

Sitagliptin sodium

According to the production method in the prior art, Chiglitazar sodium with purity of more than 99% can be obtained, and the process thereof is smooth and controllable, suitable for industrial production. However, the inventors unexpectedly found that as shown in HPLC analysis (column, $C_{18}$ column, Shim-pack VP-ODS 5 μm 250 L×4.6; mobile phase, methanol-water-tetrahydrofuran-acetic acid 40:30:30:0.5; detection wavelength, 236 nm; flow rate, 1.5 mL/min), there is always an impurity with unknown structure at the relative retention time of about 2.4, and the content of the impurity fluctuates within a range with the changes of relative ratio of raw material 1 and raw material 2. When the ratio of raw material 1 to raw material 2 is 1:1, the content of this impurity is about 0.18% (area normalization method); when the ratio of raw material 1 to raw material 2 is 1:1.5, the content of this impurity is about 0.06% (area normalization method). Since the existence and structure of this impurity have not been disclosed and reported in the prior art, the pharmacological and toxicological properties thereof are also unknown, it poses a risk to safety of the drug. In addition, since the structure of this impurity is unknown, and there is not public report about the information and separation method of impurities in Chiglitazar sodium, it is extremely difficult to separate and identify this impurity.

On one hand, in order to ensure the drug safety for patients, it is necessary to identify the structure of the unknown impurity; on the other hand, it is necessary to find the method for producing the impurity compound and obtain a control or standard substance thereof, which can be used for quality control of a drug such as Chiglitazar or Chiglitazar sodium, especially used as a control or standard substance for the detection of related substances/impurities.

SUMMARY

Based on the above needs in the prior art, one object of the present disclosure is to identify the above-mentioned compound with an unknown structure present in a drug such as Chiglitazar or Chiglitazar sodium prepared by a process described in the prior art.

The inventors have found that the impurity is sodium 3-(4-(2-(9H-carbazole-9-yl)ethoxy)phenyl)-2-((2-(4-(4-(2-sodium formate-2-((2-(4-fluorobenzoyl)pheniyl)amino)ethyl)phenoxy)benzoyl)phenyl)amino)propionate, and the structure of which is represented by formula (I):

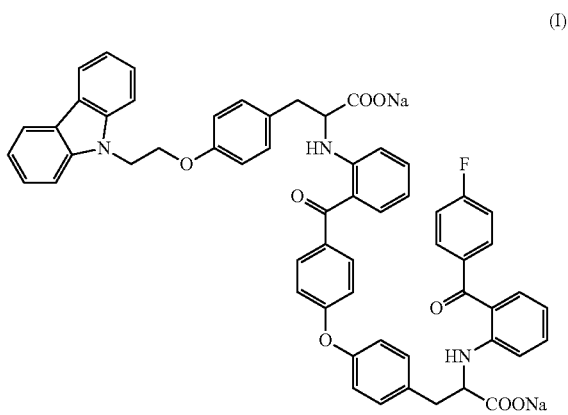

Without being bound by any theory, after extensive study and tests, the inventors hypothesized that the compound of formula (I) may be produced by the following side reactions:

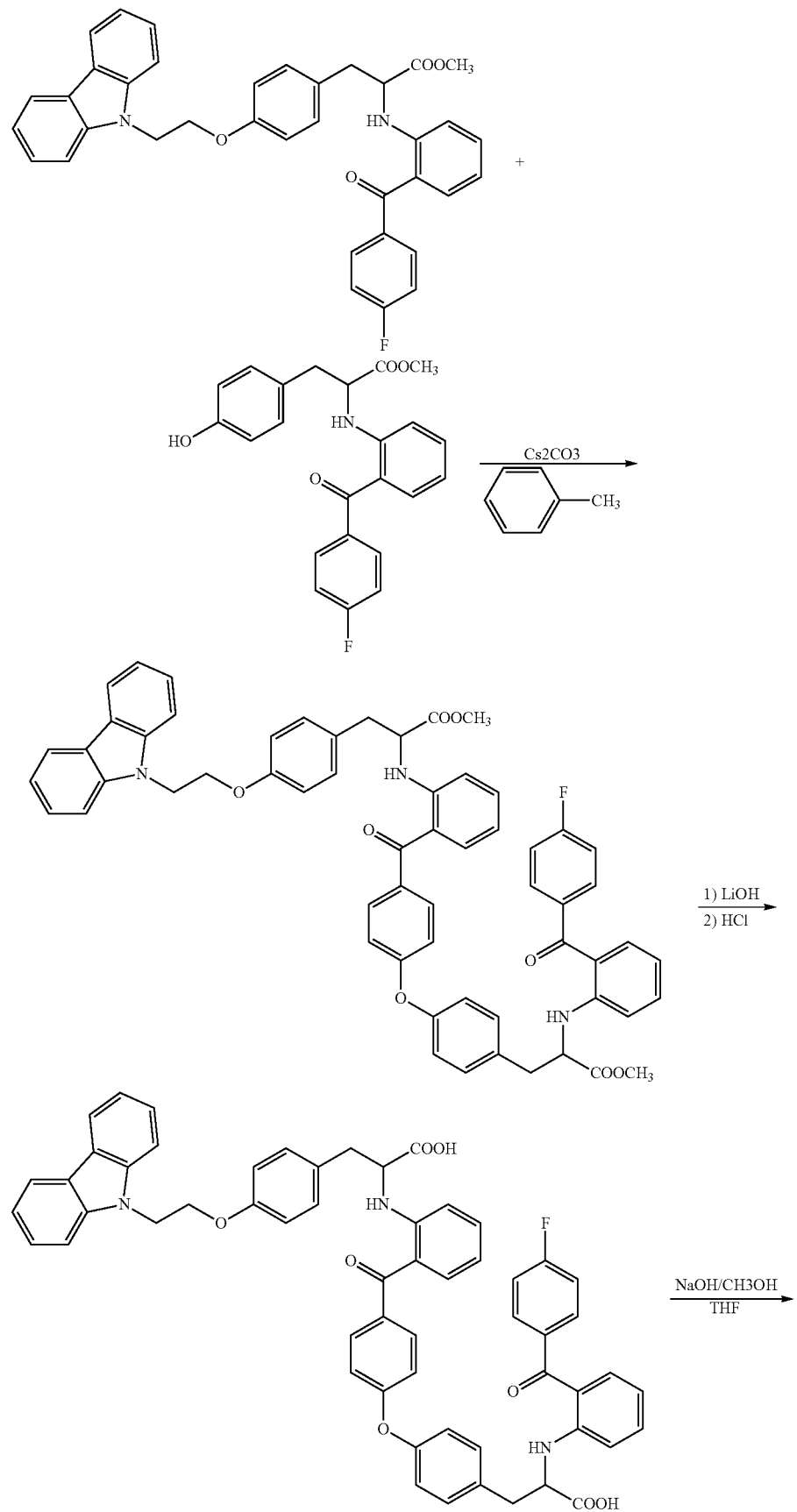

-continued

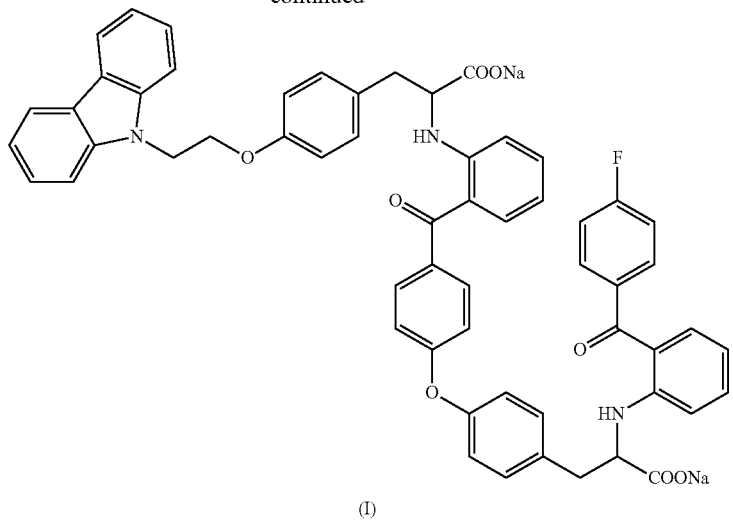

(I)

In fact, the production of the compound of formula (I) is not limited to the above-described reaction scheme during the preparation of Chiglitazar sodium, it may also present in the synthesis of Chiglitazar.

Another object of the present disclosure to provide a method for producing the compound of formula (I), an exemplary synthetic route of the method is as follows:

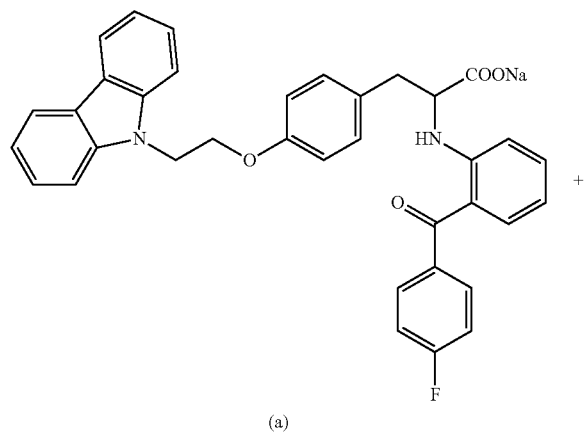

(a)

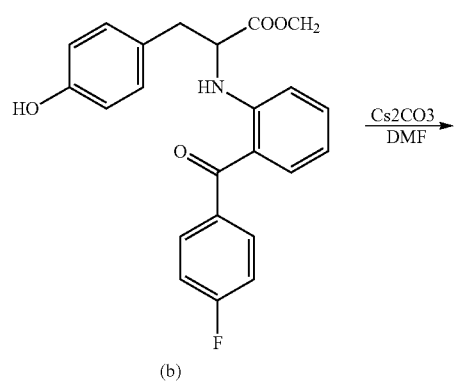

(b)

-continued
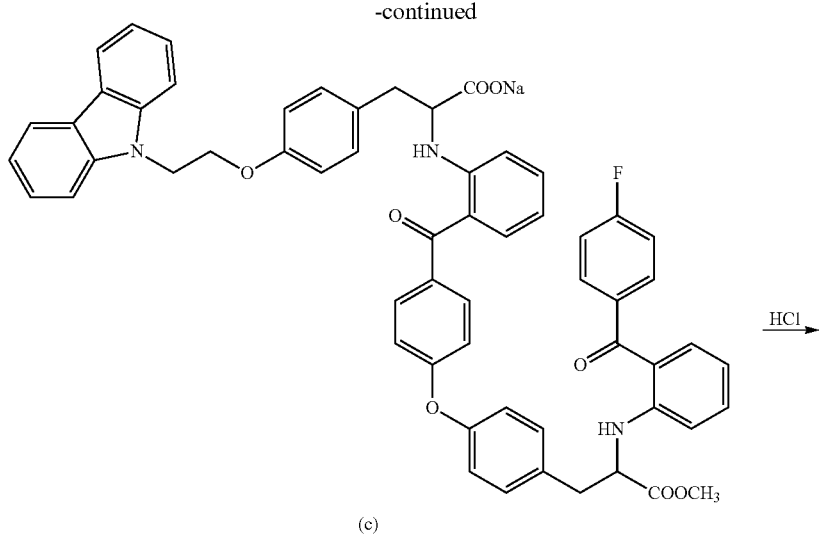
(c)
HCl →
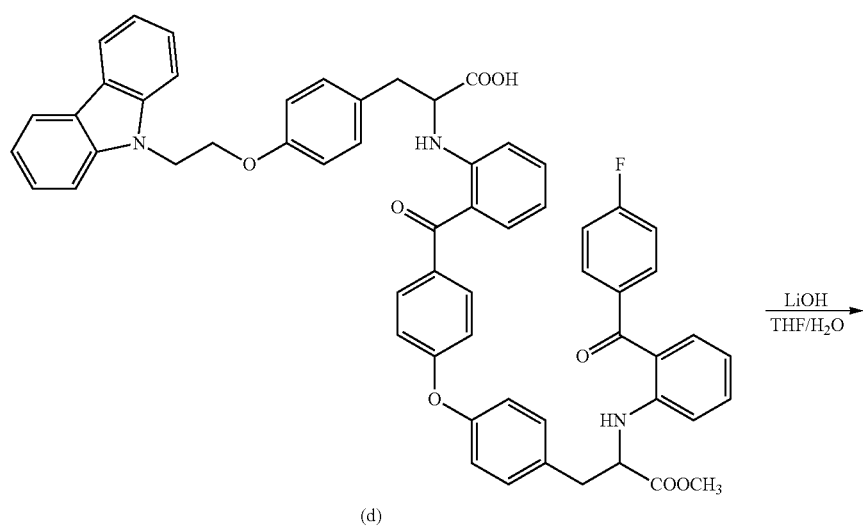
(d)
LiOH
THF/H₂O →
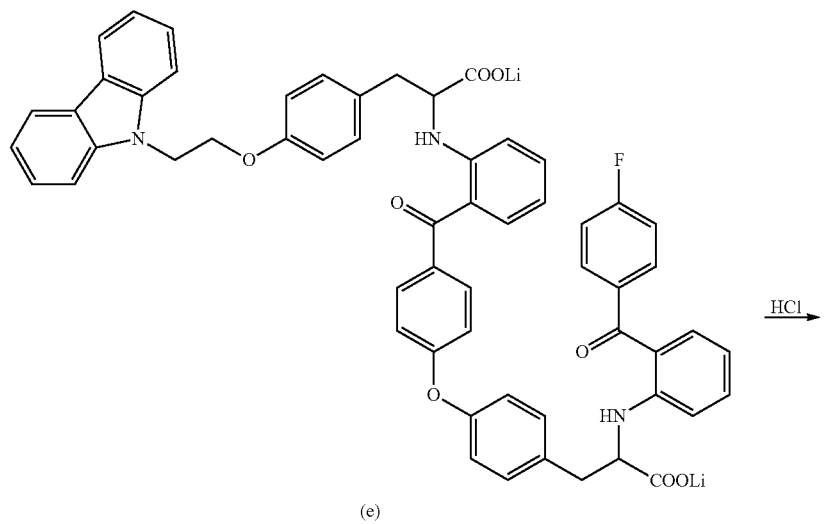
(e)
HCl →

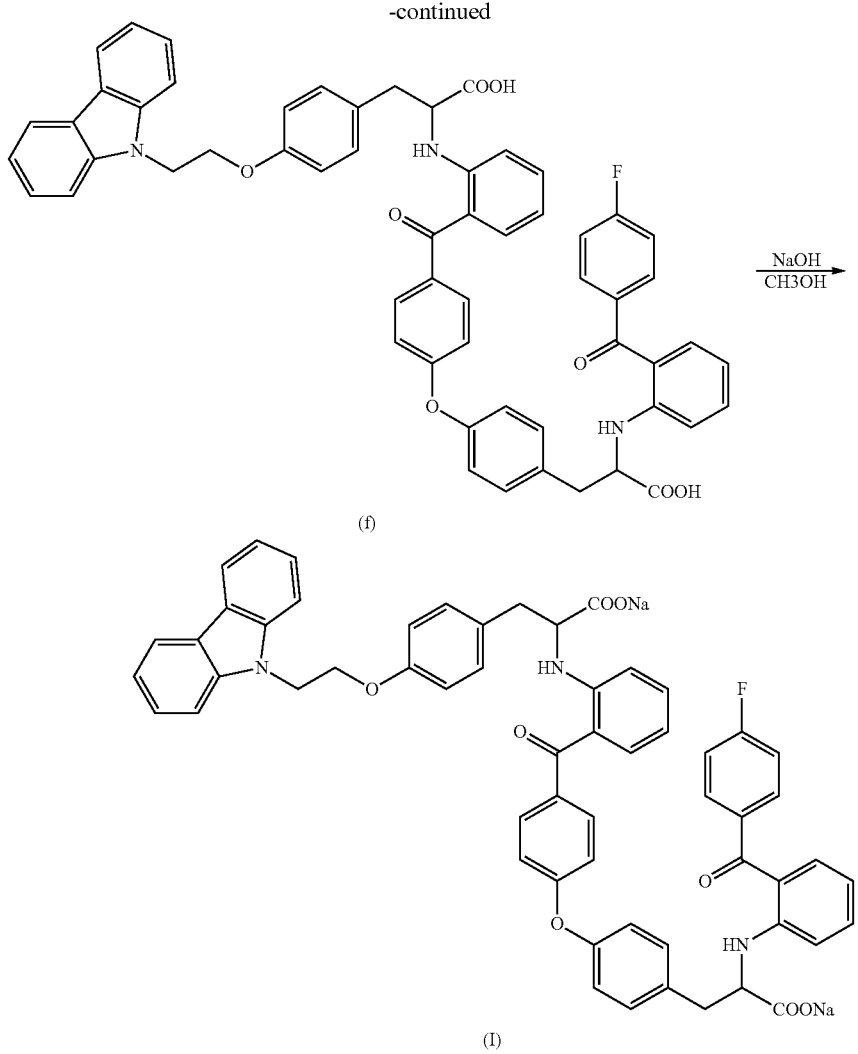

It should be noted that the reaction solvent and the base used in the above reaction scheme are all illustrative and not limiting, and those skilled in the art can make appropriate modifications and adjustments.

In an exemplary embodiment, compound (a) is subjected to a condensation reaction with compound (b) to give compound (c). The reaction can be carried out using cesium carbonate as a catalyst, preferably, N,N-dimethylformamide is used as a solvent, and the reaction temperature may be 80° C. to 120° C., the reaction time may be 20 to 30 hours. The obtained crude product can be used for next step without further purification.

Compound (c) is subjected to acidification to give compound (d). The acidification is carried out preferably with hydrochloric acid. The reaction is carried out preferably using ethyl acetate and water as a solvent, the reaction temperature may be room temperature, and the reaction time may be 4 to 5 hours. The obtained crude product can be used for next step without further purification.

Compound (d) is subjected to hydrolysis in the presence of lithium hydroxide to give compound (e). The reaction is carried out preferably using tetrahydrofuran and water as a solvent, the reaction temperature may be room temperature, and the reaction time may be 12 to 16 hours. The obtained crude product can be used for next step without further purification.

Compound (e) is subjected to acidification to give compound (f). The acidification is carried out preferably with hydrochloric acid. The reaction is carried out preferably using ethyl acetate and water as a solvent, the reaction temperature may be room temperature, and the reaction time may be 4 to 5 hours. In an exemplary embodiment, the obtained crude product is separated by a semi-preparative liquid chromatography column (column, YMC-Pack ODS-AQ 5 μm 250 L×20; mobile phase, methanol-water-tetrahydrofuran-glacial acetic acid 48:22:30:0.5; detection wavelength, 236 nm; flow rate, 8 mi/min) to give compound (f) with purity of more than 97%.

Compound (f) is neutralized with sodium hydroxide to give compound of formula (I). The reaction can be carried out using methanol as a solvent, the reaction temperature may be room temperature, and the reaction time may be 20 to 40 minutes.

In another aspect, the present disclosure also provides the use of the compound of formula (I) for quality control of a bulk drug or formulation of Chiglitazar or a derivative thereof. In particular, the present disclosure provides the use of the compound of formula (I) as a control or standard substance for the detection of impurities or related substances in Chiglitazar or Chiglitazar sodium drugs.

Accordingly, the present disclosure provides a method for quality control of a bulk drug or formulation of Chiglitazar or a derivative thereof, comprising using the compound of formula (I) of the present disclosure as a control or standard substance for the detection of the impurity or related substances.

Furthermore, the present disclosure provides a method for detecting the content of the impurity or related substances in Chiglitazar or a derivative drug thereof, comprising using the compound of formula (I)

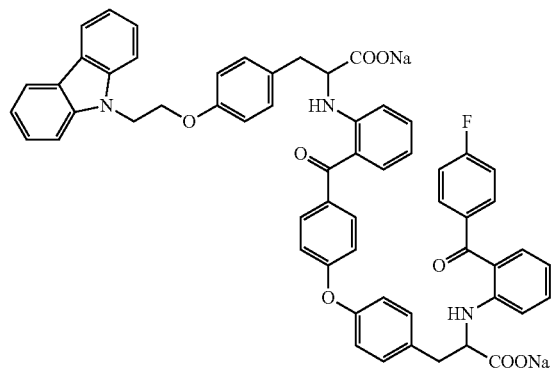

(I)

as a control or standard substance.

Preferably, the above detection method is preferably an HPLC method.

In an exemplary embodiment of the present disclosure, the condition of HPLC is as follows:

Column, $C_{18}$ column, Shim-pack VP-ODS 5 μm 250 L×4.6;

Mobile phase, methanol-water-tetrahydrofuran-acetic acid 40:30:30:0.5;
Detection wavelength, 236 nm; flow rate, 1.5 mL/min.

When the compound of formula (I) is used as the control substance, an appropriate amount of the compound of formula (I) is added to sirvastatin sodium sample solution, and the chromatogram is recorded to confirm that the compound of formula (I) is the impurity having a relative retention time of about 2.4. Record the chromatograms of the Chiglitazar sodium sample solution and the standard solution of the compound of formula (I), and calculate the content of the compound of formula (I) in the Chiglitazar sodium drug by an external standard method.

The above HPLC detection method has advantages such as accurate and reliable detection result, strong specificity, good utility, which can effectively detect the above impurity, and the impurity can be well separated from Chiglitazar or a salt thereof.

Impurity research is an important part of drug research and development through the drug research and development process, which directly affects quality and safety of a drug. In order to provide a standard substance of the related substances for quality research of Chiglitazar or a derivative thereof, improve quality standards of Chiglitazar or a derivative thereof, and compositions (including pharmaceutical preparations) containing Chiglitazar or a derivative thereof, provide important guidance for drug safety, the present disclosure identifies, studies and synthesizes the impurity generated during the process.

DETAILED DESCRIPTION

The content of the present disclosure is further described below with reference to the embodiments, but the scope of the present disclosure is not limited to these embodiments. The percentages stated in the present disclosure are all percentages by weight unless otherwise specified. The ranges of values, such as unit of measurement or percentage, described in the specification are all intended to provide an unambiguous written reference. Those skilled in the art can still obtain desired results based on teachings and principles of the present disclosure, using temperatures, concentrations, amounts, etc. outside of the range or different from the single value.

Terms and Definitions

"Derivative": In the present disclosure, a Chiglitazar derivative includes not only the Chiglitazar free acid but also a salt thereof, such as an inorganic salt such as a sodium salt, and a hydrate thereof.

"Impurity" and "relative retention time/relative retention value": Any substance that affects purity of a drug is referred to as an impurity. In general, an impurity refers to a chemical substance other than the active pharmaceutical ingredients introduced or generated during production and storage. It is well known to those skilled in the art that secondary products, side products, and additional reagents (collectively referred to as "impurities") can be identified using spectrometry methods and by other physical methods, such that the impurities are associated with peak positions in the chromatogram (or spots on a thin layer chromatography plate) (Strobel, H A; Heineman, W R, Chemical Instrumentation: Asystematic Approach, 3rd. (Wiley & Sons: New York 1989)). Thereafter, impurities can be identified by their position in the chromatogram. The position in the chroratogram is usually calculated in minutes by the time between the sample is injected onto the column and the specific component flows out through the detector, which is referred to as "retention time". This time often varies based on the setting when using the instruments and many other factors. To reduce the effects of such varies on the accuration of impurity identification, "relative retention time" (or relative retention value) is used to identify impurities. The relative retention time of an impurity is the ratio of the retention time of this impurity divided by the retention time of a reference marker (e.g., a control or standard substance).

"Control" and "standard substance": as those skilled in the pharmaceutical field know, a compound in highly pure state can be used as a "standard substance" or "control". Control substances generally refer to standard substances used for identification, inspection, content determination and calibration of the performance of a verification instrument, while standard substances generally are used for biological assays, determination of the content or titer for antibiotics or biopharmaceuticals. In the present disclosure, these two terms are exchangeable. Standard substances can be used for qualitative analysis as well as quantitative determination of the content of a compound to be detected in an unknown mixture. Standard substances are "external standard compounds" when standard substance solutions with known concentrations are used for analyzing unknown mixtures by the same technique. The content of the compound in a mixture can be determined by comparing the response values of the detector. See also U.S. Pat. No. 6,333,198, the content of which is incorporated herein by reference. If the "response factor", which compensates the sensitivity difference of the detector for two compounds, has been predetermined, the standard substance can also be used to measure the content of another compound in the mixture. When standard substance is added directly into the mixture, it is referred to as "internal standard substance". A standard substance can be used as an internal standard substance when the standard substance is not intentionally added but a method known as "standard addition" is used to make the unknown mixture contain a detectable amount of the standard substance.

Starting Materials and Test Instruments

Chiglitazar sodium: prepared according to the method of Chinese Patent Application Nos. 201410856282.5 and 201610855107.3, purity >99%.

Methyl 2-[(2-(4-fluorobenzoyl)phenyl)amino]-3-(4-hydroxyphenyl)propionate (compound (b)): produced by Beijing Lewei Taike Pharmaceutical Technology Co., Ltd., purity >96%.

High performance liquid chromatography, Instrument, UltiMate 3000; colmn, $C_{18}$ column, Shim-pack VP-ODS 5 μm 250 L×4.6; detector, VWD-3100.

Semi-preparative liquid chromatography, Instrument, UltiMate 3000; column, YMC-Pack ODS-AQ 5 μm 250 L×20; detector, VWD-3100.

Proton magnetic resonance, Instrument, Varian INOVA 500; solvent, DSO-$d_6$.

High resolution mass spectrum, Instrument, VG ZAB-HS chromatograph-mass spectrometer; detection method, fast atom bombardment ionization (FAB).

Example 1: Separation, Preparation and Identification of Compound of Formula (I)

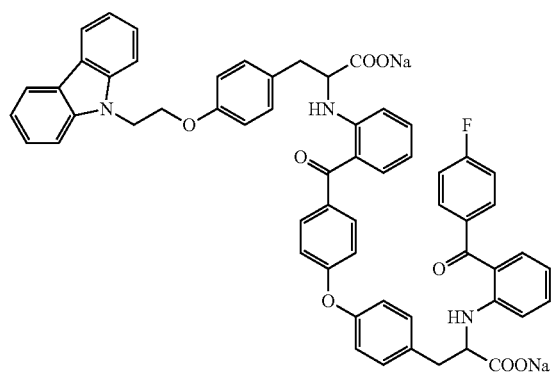

(I)

1. Separation 0.5 g of Chiglitazar sodium (prepared according to the method of Chinese Patent Application Nos. 201410856282.5 and 201610855107.3) was separated by a semi-preparative liquid chromatography column (column, YMC-Pack ODS-AQ 5 μm 250 L×2; mobile phase, methanol-water-tetrahydrofuran-glacial acetic acid 48:22:30:0.5; detection wavelength, 236 nm; flow rate, 8 ml/min), the effluent between 30 and 42 minutes was collected, and then neutralized to pH 7 with a 1 mol/L aqueous sodium bicarbonate solution. The above separation operation was repeated 40 times, and the liquid after each neutralization was combined. The solution combined was concentrated under vacuum to remove the organic solvent, and neutralized to pH 5-6 with a 1 mol/L diluted hydrochloric acid.

Then the mixture was filtered, and the obtained solids were washed with water, then collected and dried under vacuum at room temperature for 24 hours to give 5 mg of compound (f), with purity of 97.8% (HPLC), LC-MS (m/z) 933 (M+1).

To a reaction flask, 5 mg (0.0054 mmol) of compound (f) and 1 mL of methanol were successively added, followed by stirring to dissolve. 0.43 mg (0.011 mmol) of sodium hydroxide was dissolved in 0.5 ml of methanol, and the mixture was added dropwise to the above solution, stirred at room temperature for 30 minutes. Afterwards, the reaction solution was added dropwise to 15 mL of anhydrous diethyl ether, and the mixture was filtered, then the solids obtained were dried under vacuum at 60° C. for 8 h to give 5 mg of compound of formula (I), with purity of 98.4% (HPLC).

Structure Identification

HRMS (M$^+$+1) ($C_{58}H_{45}N_3O_8FN_2$), calculated (%): 976.2986; found (%): 976.2992.

$^1$H NMR (DMSO-$d_6$) δ 2.87 (one of dd, 1H, $CH_2$), 3.02 (one of dd, 1H, $CH_2$), 3.05 (one of dd, 1H, $CH_2$), 3.22 (one of dd, 1, $C_2$), 3.91 (m, 1H, CH), 4.06 (m, 1H, CH), 4.24 (t, 2H, $CH_2$), 4.71 (t, 2H, $CH_2$), 6.40 (m, 2H, Ar—H), 6.58 (d, 2H, Ar—H), 6.65 (d, 1H, Ar—H), 6.69 (d, 1H, Ar—H), 6.90 (d, 4H, Ar—H), 7.00 (d, 2H, Ar—H), 7.17 (t, 2H, Ar—H), 7.27 (m, 8H, Ar—H), 7.42 (m, 2H, Ar—H), 7.47 (m, 2H, Ar—H), 7.57 (m, 2H, Ar—H), 7.62 (d, 2H, Ar—H), 8.11 (d, 2H, Ar—H), 8.60 (d, 1H, NH), 8.81 (dd, 1H, NH).

2. Preparation

To a reaction flask, 400 mL of N,N-dimethylformamide, 23.76 g (40 mmol) of sodium 2-(2-(4-fluorobenzoyl)phenylamino)-3-(4-(2-(9H-carbazole-9-yl)ethoxy)phenyl)propionate (i.e., compound (a)), 19.65 g (50 mmol) of methyl 2-[(2-(4-fluorobenzoyl)phenyl)amino]-3-(4-hydroxyphenyl)propionate (i.e., compound (b)), and 16.25 g (50 mmol) of cesium carbonate were sequentially added. The reaction mixture was allowed to react at 120° C. for 25 h, then filtered. The filtrate was added to 4000 mL of saturated sodium chloride solution, then the mixture was filtered, and the solids obtained were washed with water and collected, and dried under vacuum to give a crude product of compound (c), with purity of 12.2% (HPLC), LC-MS (m/z) 969 (M+1). The obtained product was used for next step without further purification.

To a reaction flask, 400 mL of ethyl acetate and the above compound (c) were successively added. The reaction mixture was stirred for 30 minutes, then 230 ml of water was added, and 150 mL of 3 mol/L of dilute hydrochloric acid was added dropwise. The reaction mixture was stirred for another 4 hours, and the organic phase was separated and concentrated under vacuum to give a crude product of compound (d). The obtained product was used for next step without further purification.

The above compound (d) was dissolved in 350 mL of tetrahydrofuran. Then 48 mL of 12 mol/L aqueous lithium hydroxide solution was added. The reaction mixture was stirred at room temperature for 14 hours. The organic phase was separated and concentrated under vacuum to give a crude product of compound (e). The obtained product was used for next step without further purification.

To a reaction flask, 480 mL of ethyl acetate and the above compound (e) were successively added. The reaction mixture was stirred for 30 minutes, then 230 mL of water was added, and 150 mL of 3 mol/L of dilute hydrochloric acid was added dropwise. The reaction mixture was stirred for another 4 hours, and the organic phase was separated and concentrated under vacuum to give a crude product of compound (f), with purity of 18.9% (HPLC), LC-MS (m/z) 933 (M+1).

0.5 g of the crude product of compound (d) was loaded to a semi-preparative liquid chromatography column (column, YMC-Pack ODS-AQ 5 μm 250 L×20; mobile phase, methanol-water-tetrahydrofuran-glacial acetic acid 48:22:30:0.5; detection wavelength, 236 nm; flow rate, 8 ml/min), the effluent between 30 and 42 minutes was collected, and then neutralized to pH 7 with a 1 mol/L aqueous sodium bicarbonate solution. The above separation operation was repeated 5 times, and the liquid after each neutralization was combined. The solution combined was concentrated under vacuum to remove the organic solvent, and neutralized to pH 5-6 with a 1 mol/L diluted hydrochloric acid. Then the mixture was filtered, and the solids obtained were washed with water, then collected and dried under vacuum at room temperature for 24 hours to give 230 mg of compound (f), with purity of 98.0% (HPLC), LC-MS (m/z) 933 (M+1).

To a reaction flask, 230 mg (0.247 mmol) of compound (f) and 5 mL of methanol were successively added, followed by stirring to dissolve. 19.76 mg (0.494 mmol) of sodium hydroxide was dissolved in 1 mL of methanol, and added dropwise to the above solution, stirred at room temperature for 30 minutes. Afterwards, the reaction solution was added dropwise to 45 mL of anhydrous diethyl ether, and the mixture was filtered, then the solids obtained were dried under vacuum at 60° C. for 8 h to give 236 mg of compound of formula (I), with purity of 98.6% (HPLC).

The structure identification showed that the obtained compound was consistent with the separated compound in HRMS and $^1$H NMR features.

Example 2: Compound of Formula (I) as a Control for Content Determination of Impurity in Chiglitazar Sodium Drug 1. Test Condition Instrument, UltiMate 3000; column, C$_{18}$ column, Shim-pack VP-ODS 5 μm L 250 L×4.6; detector, VWD-3100; mobile phase, methanol-water-tetrahydrofuran-acetic acid 40:30:30:0.5; detection wavelength, 236 no; flow rate, 1.5 mL/min.

2. Test Method (1) 10 mg of Chiglitazar sodium sample was accurately weighed, and put into a 100 ml volumetric flask, then dissolved with a solvent of methanol-water-tetrahydrofuran (40:30:30) and made up to the scale. The solution obtained was mixed well until homogeneous, which was used as test solution A. 20 μl of solution A was accurately pipetted and injected into a liquid chromatograph, then the chromatogram was recorded.

(2) 10 mg of compound of formula (I) was accurately weighed, and put into a 100 ml volumetric flask, then dissolved with a solvent of methanol-water-tetrahydrofuran (40:30:30) and the volume was filled up to the marking. The solution obtained was mixed well until homogeneous. 1 mL to the solution was accurately pipetted into a 100 mi volumetric flask, then dissolved with a solvent of methanol-water-tetrahydrofuran (40:30:30) and the volume was filled up to the marking. The solution obtained was mixed well until homogeneous, which was used as test solution B. 20 μl solution B was accurately pipetted and injected into a liquid chromatograph, then the chromatogram was recorded.

(3) 0.5 mL of test solution A and 0.5 mL of test solution B were pipetted respectively and mixed well until homogeneous. The obtained solution was used as test solution C. 20 μl solution C was accurately pipetted and injected into a liquid chromatograph, then the chromatogram was recorded.

3. Test Results

In the chromatogram of test solution A, the peak of Chiglitazar sodium was at 15.1 min, there was an impurity peak at 35.8 min, and the relative area was 0.05%.

In the chromatogram of test solution B, the peak of the compound of formula (I) was at 35.8 min.

In the chromatogram of test solution C, the peak of Chiglitazar sodium was at 15.1 min, there was an impurity peak at 35.8 min, and the relative area was 0.7%.

Conclusion: the compound of formula (I) was confirmed to be the impurity having a relative retention time about 2.4 in Chiglitazar sodium sample.

Example 3: Compound of Formula (I) as a Standard Substance for Content Determination of Impurity in Chiglitazar Sodium Drug 1. Test Condition Instrument, UltiMate 3000; column, C$_{18}$ column, Shim-pack VP-ODS 5 μm 250 L×4.6; detector, VWD-3100; mobile phase, methanol-water-tetrahydrofuran-acetic acid 40:30:30:0.5; detection wavelength, 236 no; flow rate, 1.5 mL/min.

2. Test Method 10 mg of Chiglitazar sodium sample was accurately weighed, and put into a 100 ml volumetric flask, then dissolved with a solvent of methanol-water-tetrahydrofuran (40:30:30) and the volume was filled up to the marking. The solution obtained was mixed well until homogeneous, which was used as test solution. Additionally, 10 mg of standard substance of the compound of formula (I) was accurately weighed, and put into a 100 ml volumetric flask, then dissolved with a solvent of methanol-water-tetrahydrofuran (40:30:30) and the volume was filled up to the marking. The solution obtained was mixed well until homogeneous. 1 mL solution was accurately pipetted into a 1000 ml volumetric flask, then dissolved with a solvent of methanol-water-tetrahydrofuran (40:30:30) and the volume was filled up to the marking. The solution obtained was mixed well until homogeneous, which was used as control solution. 20 μl of each of the above two solutions was accurately pipetted and injected into a liquid chromatograph, then the chromatogram was recorded. The content of the compound of formula (I) in Chiglitazar sodium sample was calculated according to peak area by external standard method.

3. Test Results

Three batches of Chiglitazar sodium were tested, and the results were shown in Table 1.

TABLE 1

Content of the compound of formula (I) in Chiglitazar sodium sample

| Chiglitazar sodium sample | Content of the compound of formula (I) (%) |
| --- | --- |
| Batch 20160817 | 0.07 |
| Batch 20160909 | 0.08 |
| Batch 20160923 | 0.08 |

The invention claimed is:
1. A compound of formula (I):
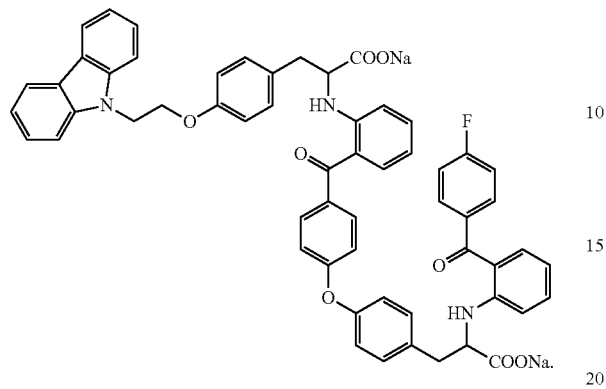
2. A method for producing the compound of formula (I) according to claim 1, comprising reacting a compound of formula (f) with sodium hydroxide:
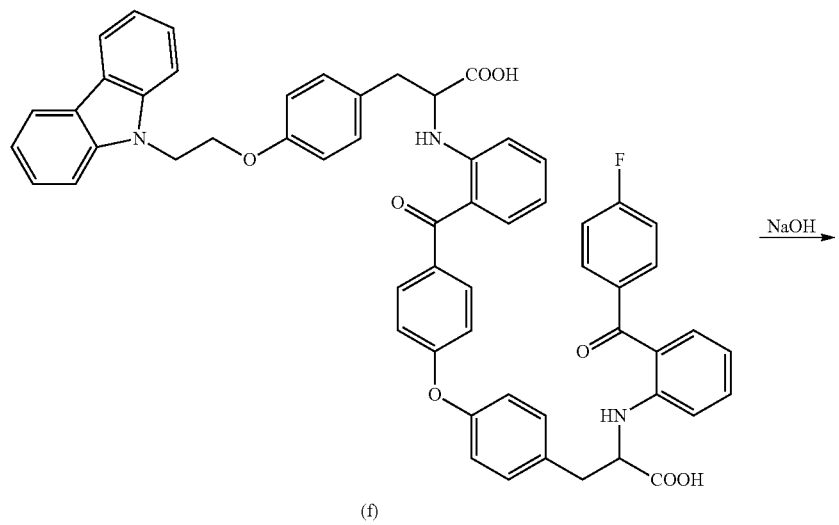

3. The method for producing the compound of formula (I) according to claim 2, wherein the compound of formula (f) is obtained by acidification of a compound of formula (e):
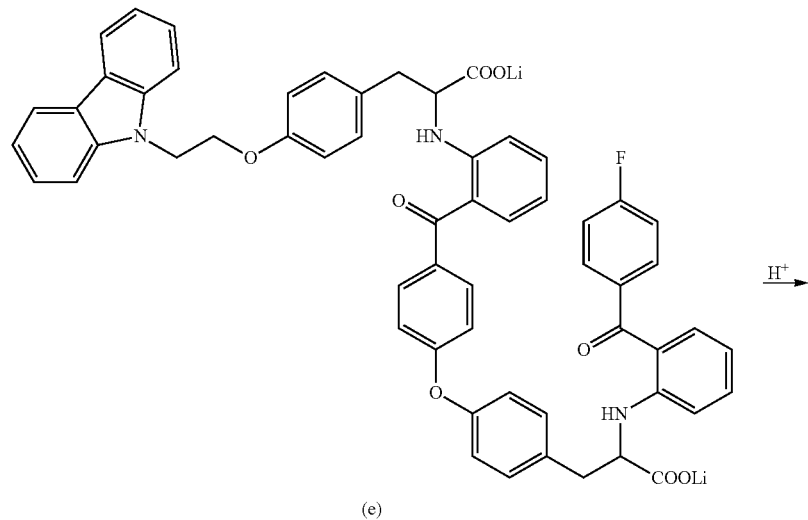
(e)
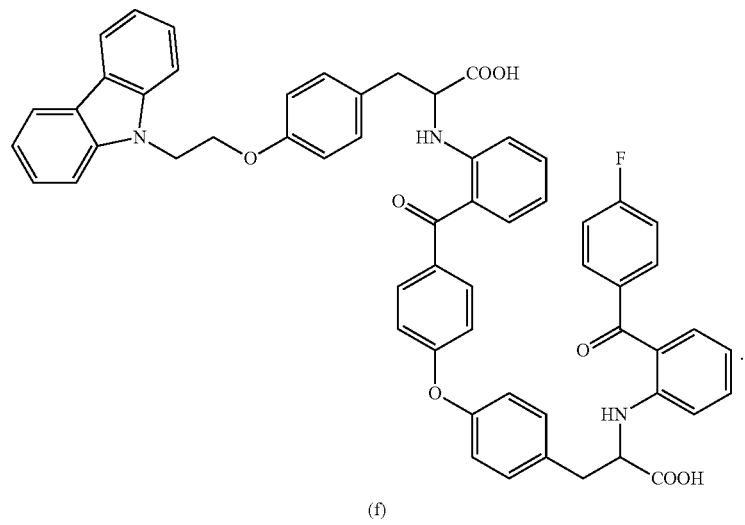
(f)

4. The method for producing the compound of formula (I) according to claim 3, wherein the compound of formula (e) is obtained by reacting a compound of formula (d) with lithium hydroxide:
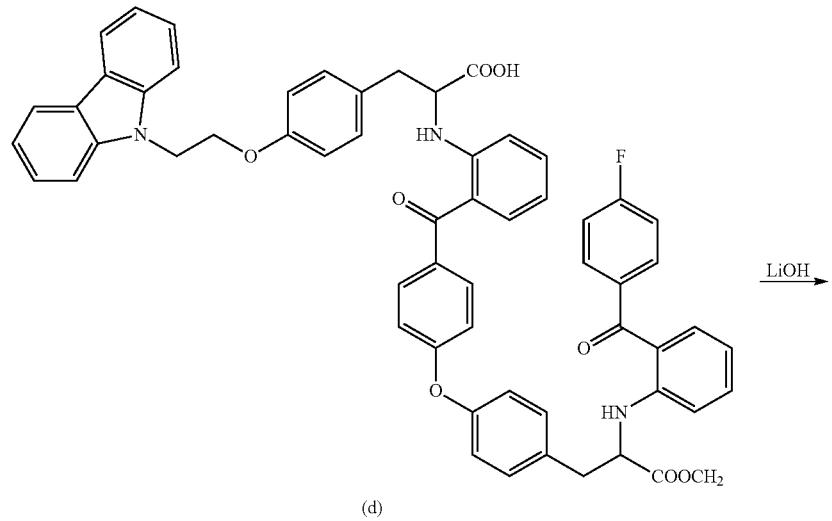
(d)
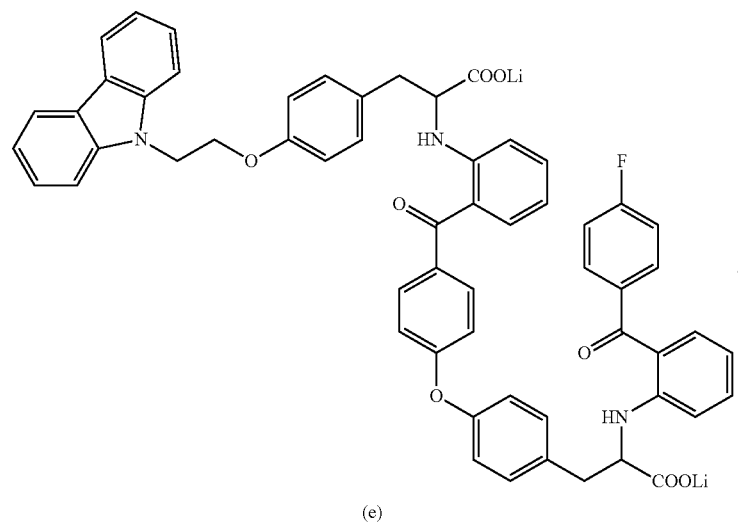
(e)

5. The method for producing the compound of formula (I) according to claim 4, wherein the compound of formula (d) is obtained by acidification of a compound of formula (c):
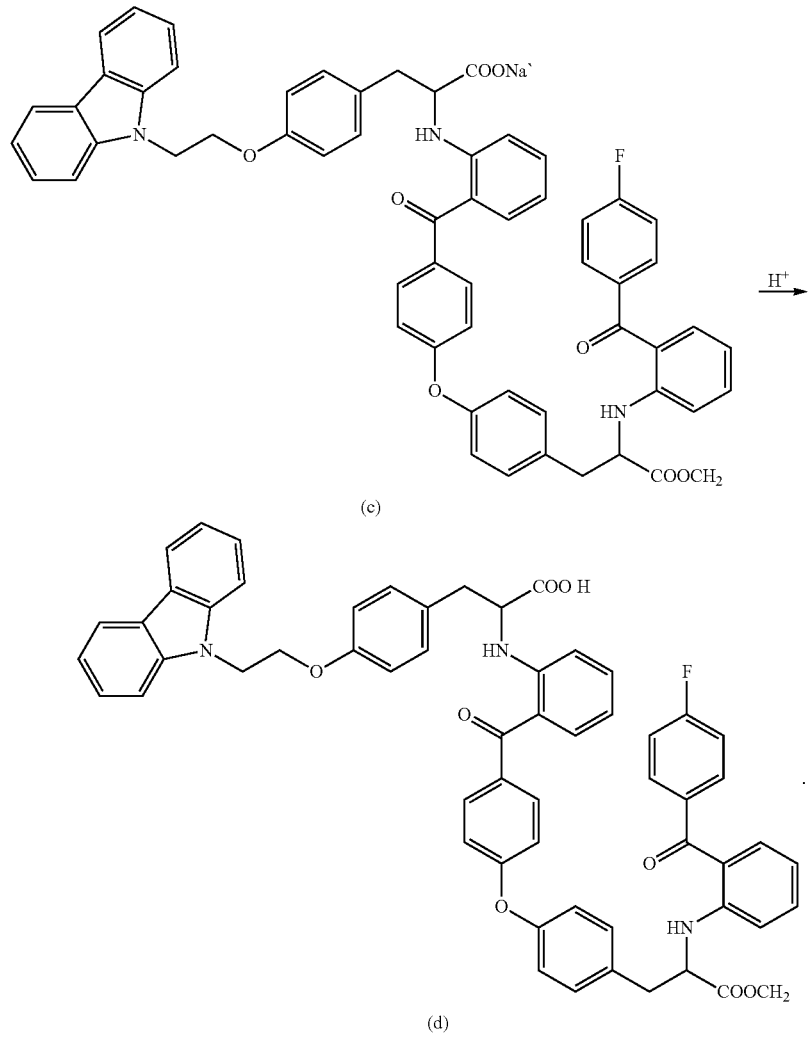
6. The method for producing the compound of formula (I) according to claim 5, wherein the compound of formula (c) is obtained by reacting a compound of formula (a) with a compound of formula (b):
-continued
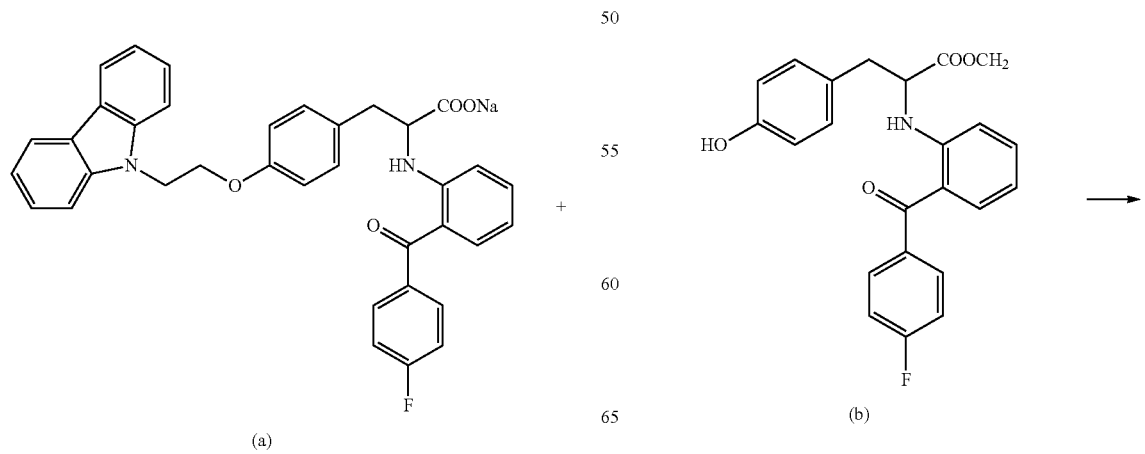

-continued

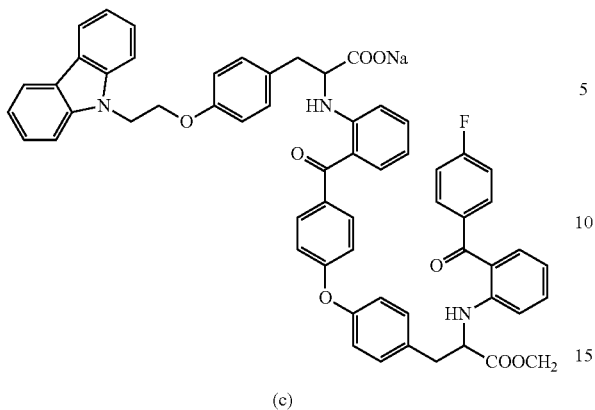

(c)

7. A method for detecting the content of the impurity in Chiglitazar or sodium salt thereof, comprising using a compound of formula (I)

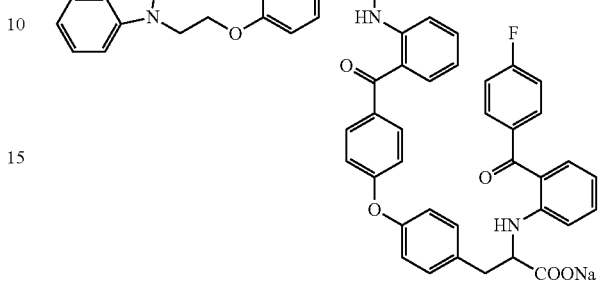

as a control or standard substance.

8. The method according to claim 7, which is a method of HPLC, wherein the compound of formula (I)

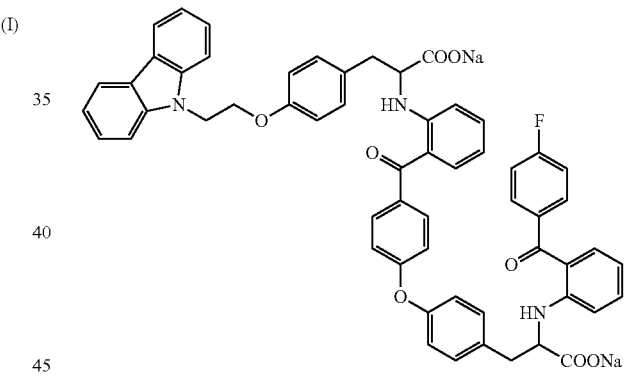

is used as an external standard, and the detection condition is: column, $C_{18}$ column; mobile phase, methanol-water-tetrahydrofuran-acetic acid 40:30:30:0.5; detection wavelength, 236 nm.

9. A method for quality control in a synthesis of Chiglitazar or a derivative thereof, comprising using a compound of formula (I)

(I)

for the detection or control of the content of the impurity or related substances.

* * * * *